US 6,690,965 B1

(12) United States Patent
Riaziat et al.

(10) Patent No.: US 6,690,965 B1
(45) Date of Patent: Feb. 10, 2004

(54) METHOD AND SYSTEM FOR PHYSIOLOGICAL GATING OF RADIATION THERAPY

(75) Inventors: Majid L. Riaziat, San Jose, CA (US); Stanley Mansfield, Sunnyvale, CA (US); Hassan Mostafavi, Los Altos, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 09/712,724

(22) Filed: Nov. 14, 2000

Related U.S. Application Data

(63) Continuation of application No. 09/178,384, filed on Oct. 23, 1998, now abandoned.

(51) Int. Cl.[7] .............................. A61B 5/05; A61B 6/00
(52) U.S. Cl. ..................... 600/428; 600/407; 600/427; 600/429; 378/62; 378/65; 378/69; 606/130
(58) Field of Search ................................. 600/407, 587, 600/411, 428, 473, 476, 477, 437, 427, 429, 413, 426, 534, 538, 529, 301; 606/130; 250/349, 358.1, 363.02; 378/65, 62, 69, 205; 345/619–634

(56) References Cited

U.S. PATENT DOCUMENTS

| | | | |
|---|---|---|---|
| 3,861,807 A | 1/1975 | Lescrenier .................. 356/152 |
| 3,871,360 A | 3/1975 | Van Horn et al. ...... 128/2.05 R |
| 4,031,884 A | 6/1977 | Henzel .................. 128/2.05 R |
| 4,262,306 A | 4/1981 | Renner ......................... 358/93 |
| 4,463,425 A | 7/1984 | Hirano et al. ............... 364/471 |
| 4,994,965 A | 2/1991 | Crawford et al. ...... 364/413.15 |
| 5,080,100 A | 1/1992 | Trotel ...................... 128/653.1 |
| 5,271,055 A | 12/1993 | Hsieh et al. .................. 378/95 |
| 5,279,309 A | 1/1994 | Taylor et al. ............... 128/782 |
| 5,295,483 A | 3/1994 | Nowacki et al. ....... 128/660.03 |
| 5,315,630 A | 5/1994 | Sturm et al. ................... 378/65 |
| 5,389,101 A | 2/1995 | Heilbrun et al. |
| 5,394,875 A | 3/1995 | Lewis et al. ........... 128/660.09 |
| 5,446,548 A | 8/1995 | Gerig et al. ................ 356/375 |
| 5,482,042 A | * 1/1996 | Fujita ......................... 600/428 |
| 5,538,494 A | 7/1996 | Matsuda ........................ 600/1 |
| 5,603,318 A | 2/1997 | Heilbrun et al. |
| 5,619,995 A | 4/1997 | Lobodzinski ............... 600/425 |
| 5,622,187 A | * 4/1997 | Carol ......................... 128/897 |
| 5,638,819 A | 6/1997 | Manwaring et al. ........ 600/424 |
| 5,727,554 A | * 3/1998 | Kalend et al. .............. 600/407 |
| 5,764,723 A | 6/1998 | Weinberger et al. .......... 378/65 |
| 5,784,431 A | 7/1998 | Kalend et al. |
| 5,820,553 A | * 10/1998 | Hughes ....................... 378/65 |
| 5,823,192 A | 10/1998 | Kalend et al. |
| 5,836,954 A | 11/1998 | Heilbrun et al. |

(List continued on next page.)

FOREIGN PATENT DOCUMENTS

| | | | |
|---|---|---|---|
| DE | 43 41 324 A 1 | 6/1995 | ..................... 17/22 |
| FI | 79458 | 9/1989 | |
| WO | WO 98/16151 | 4/1998 | ..................... 5/205 |

OTHER PUBLICATIONS

Jolesz, Ferenc M.D., et al.; "Image–Guided Procedures And The Operating Room Of The Future"; *Radiology; SPL Technical Report #48*; May 1997; 204:601–612.

(List continued on next page.)

*Primary Examiner*—Eleni Mantis Mercader

(57) ABSTRACT

A method and system for physiological gating for radiation therapy is disclosed. According to an aspect, the invention comprises the use of an optical or video image system to measure regular physiological movement of a patient's body. The image data can be used to quantify voluntary or involuntary motion of the patient that may affect the delivery of radiation to a target tissue. A gating signal can be generated to suspend delivery of radiation upon certain threshold event detected in the physiological movement.

53 Claims, 9 Drawing Sheets

U.S. PATENT DOCUMENTS

| | | | | |
|---|---|---|---|---|
| 5,912,656 A | | 6/1999 | Tham et al. | 345/418 |
| 5,954,647 A | * | 9/1999 | Bova et al. | 378/205 |
| 6,076,005 A | * | 6/2000 | Sontag et al. | 600/413 |
| 6,138,302 A | | 10/2000 | Sashin et al. | |
| 6,144,875 A | * | 11/2000 | Schweikard et al. | 378/69 |
| 6,146,390 A | | 11/2000 | Heilbrun et al. | |
| 6,165,181 A | | 12/2000 | Heilbrun et al. | |
| 6,185,445 B1 | | 2/2001 | Knüttel | 600/411 |
| 6,185,446 B1 | | 2/2001 | Carlsen, Jr. | 600/411 |
| 6,198,959 B1 | | 3/2001 | Wang | 600/413 |
| 6,272,368 B1 | * | 8/2001 | Alexandrescu | 250/349 |
| 6,405,072 B1 | * | 6/2002 | Cosman | 600/426 |
| 6,473,635 B1 | | 10/2002 | Rasche | 600/428 |

OTHER PUBLICATIONS

Ference A. Jolesz; "Image–Guided Procedures and the Operating Room of the Future"; Radiology; SPL Technical Report #48; May 1997; 204; 601–612.

Peltola, Seppo M.Sc.; "Gated Radiotherapy To Compensate For Patient Breathing"; *Proceedings of the Eleventh Varian Users Meeting*; Marco Island, Florida; May 11–13, 1986.

Mah, Katherine, et al.; "Time Varying Dose Due To Respiratory Motion During Radiation Therapy Of the Thorax"; *Proceedings of the Eighth Int'l Conference on the Use of Computers In Radiation Therapy*; Toronto, Canada; Jul. 9–12, 1984; pp. 294–298.

Mori, Masayuki, et al.; "Accurate Contiguous Sections Without Breath–Holding On Chest CT: Value of Respiratory Gating and Ultrafast CT"; *AJR*:162, May 1994; pp. 1057–1062.

Robinson, Gary D., et al.; "Ghosting of Pulmonary Nodules With Respiratory Motion: Comparison of Helical and Conventional CT Using an In Vitro Pediatric Model"; *AJR:167*; Nov. 1996; pp. 1189–1193.

Li, Debiao, et al.; "Coronary Arteries: Three–dimensional MR Imaging With Retrospective Respiratory Gating"; *Radiology*; Dec. 1996; vol. 201; No. 3; pp. 857–863.

Kachelriess, Marc, et al.; "Electrocardiogram–correlated Image Reconstruction From Subsecond Spiral Computed Tomography Scans Of The Heart"; *Med. Phys.* 25(12); Dec. 1998; pp. 2417–2431.

Tada, Takuhito, et al.; "Lung Cancer: Intermittent Irradiation Synchronized With Respiratory Motion–Results Of A Pilot Study"; *Radiology*; Jun., 1998; vol. 207; No. 3; pp. 779–783.

Solberg, Timothy D., et al.; "Feasibility of Gated IMRT"; 3 pps.

Wong, John W., et al.; "The Use Of Active Breathing Control (ABC) To Reduce Margin For Breathing Motion"; *Int. J. Radiation Oncology Biol. Phys.*; 1999; vol. 44; No. 4; pp. 911–919.

Mageras, Gig, et al., "Initial Clinical Evaluation Of A Respiratory Gating Radiotherapy System"; *Dept. of Medical Physics, Memorial Sloan–Kettering Cancer Center*, New York; 4 pps.

Yorke, Ellen, et al.; "Respiratory Gating Of Sliding Window IMRT"; *Dept. of Medical Physics, Memorial Sloan–Kettering Cancer Center*, New York; 4 pps.

Keatley, Eric, et al.; "Computer Automated Diaphragm Motion Quantification in a Fluroscopic Movie"; *Dept. of Medical Physics, Memorial Sloan–Kettering Cancer Center*, New York; 3 pps.

Kubo, H. Dale, et al.; "Breathing–Synchronized Radiotherapy Program at the University of California Davis Cancer Center"; *Med. Phys.* 27(2); Feb. 2000; pp. 346–353.

Iwasawa, Tae, et al.; "Normal In–Plane Respiratory Motion of the Bilateral Hemidiaphragms Evaluated By Sequentially Substracted Fast Magnetic Resonance Images"; *Journal of Thoracic Imaging*; 1999; vol. 14, No. 2; pp. 130–134.

Kim, W.S., et al.; "Extraction of Cardiac and Respiratory Motion Cycles by Use of Projection Data and Its Applications to NMR Imaging"; *Magnetic Resonance in Medicine 13*; 1990; pp. 25–37.

Woodard, Pamela K., et al.; "Detection of Coronary Stenoses on Source and Projection Images Using Three–Dimensional MR Angiography With Retrospective Respiratory Gating: Preliminary Experience"; *AJR:170*; Apr. 1998; No. 4; pp. 883–888.

Sinkus, Ralph, et al.; "Modern Pattern Adapted Real–Time Respiratory Gating"; *Magnetic Resonance in Medicine 41*; 1999; pp. 148–155.

Weiger, Markus, et al.; "Motion–Adapted Gating Based on k–Space Weighting For Reduction of Respiratory Motion Artifacts"; *Magnetic Resonance in Medicine 38*; 1997; pp. 322–333.

Wang, Yi, et al.; "Implications For The Spatial Resolution in Coronary Imaging"; *Magnetic Resonance in Medicine 33*; 1995; pp. 713–719.

Ritchie, Cameron J., et al.; "Predictive Respiratory Gating: A New Method To Reduce Motion Artifacts on CT Scans"; *Radiology*; 1994; pp. 847–852; vol. 190; No. 3.

Kubo, H. Dale, et al.; "Potential and Role of a Prototype Amorphous Silicon Array Electronic Portal Imaging Device in Breathing Synchronized Radiotherapy"; *Med. Phys.* 26(11); Nov. 1999; pp. 2410–2414.

Kubo, Hideo D., et al., "Respiration Gated Radiotherapy Treatment: A Technical Study"; *Phys. Med. Biol.* (1996) vol. 41; pp. 83–91.

J.M. Balter et al.; "Uncertainties In CT–Based Radiation Therapy Treatment Planning Associated With Patient Breathing"; *Int. J. Radiat. Oncol., Biol., Phys.* 36; pp. 167–174 (Aug. 1996).

S.C. Davies et al.; "Ultrasound Quantitation Of Respiratory Organ Motion in The Upper Abdomen"; *Br. J. Radiol.* 67; pp. 1096–1102 (Nov. 1994).

R.L. Ehman et al.; Magnetic Resonance Imaging With Respiratory Gating: Techniques and Advantages; *Am. J. Roentgenol* 143; pp. 1175–1182 (Dec. 1984).

H. Frölich et al.; "A Simple Device For Breath–Level Monitoring During CT"; *Radiology* 156; p. 235 (Jul. 1985).

R.M. Henkelman et al.; "How Important Is Breathing in Radiation Therapy Of The Thorax?"; *Int. J. Radiat. Oncol. Biol. Phys.* 8; pp. 2005–2010 (Nov. 1982).

M.B.M. Hofman et al.; "MRI Of Coronary Arteries: 2D Breath–Hold vs. 3D Respiratory–Gated Acquisition"; *J. of Comp. Assisted Tomography* 19; pp. 56–62 (Jan./Feb. 1995).

G.J. Kutcher et al.; "Control, Correction, and Modeling Of Setup Errors and Organ Motion", *Semin. Radiat. Oncol.* 5; pp. 134–145 (Apr. 1995).

J. Hanley et al.; "Deep Inspiration Breath–Hold Technique For Lung Tumors: The Potential Value of Target Immobilization And Reduced Lung Density In Dose Escalation"; *Int. J. Radiat. Oncol., Biol. Phys.* 45; pp. 603–611 (Oct. 1999).

L.S. Johnson et al.; "Initial Clinical Experience With A Video–Based Patient Positioning System"; *Int. J. Radiat. Oncol. Biol. Phys.* 45; pp. 205–213; (Aug. 1999).

H.W. Korin et al.; "Respiratory Kinematics Of The Upper Abdominal Organs: A Quantitative Study"; *Magn. Reson. Med.* 23; pp. 172–178 (Jan. 1992).

H.D. Kubo et al.; "Respiration Gated Radiotherapy Treatment: A Technical Study"; *Phys. Med. Biol.* 41; pp. 83–91; (1996).

H.D. Kubo et al.; "Potential And Role Of A Prototype Amorphous Silicon Array Electronic Portal Imaging Device In Breathing Synchronized Radiotherapy"; *Med. Phys.* 26; pp. 2410–2414; (Nov. 1999).

C.E. Lewis et al.; "Comparison Of Respiratory Triggering And Gating Techniques For The Removal Of Respiratory Artifacts In MR Imaging"; *Radiology* 160; pp. 803–810; (Sep. 1986).

D. Li et al.; "Coronary Arteries: Three–Dimensional MR Imaging With Retrospective Respiratory Gating"; *Radiology* 201; pp. 857–863 (Dec. 1996).

M.A. Moerland et al.; "The Influence Of Respiration Induced Motion Of The Kidneys On The Accuracy Of Radiotherapy Treatment Planning, A Magnetic Resonance Imaging Study"; *Radiotherapy Oncol.* 30 pp. 150–154 (1994).

K. Ohara et al.; "Irradiation Synchronized With Respiration Gate"; *Int. J. Radiat. Oncol. Biol. Phys.* 17; pp. 853–857; (Oct. 1989).

J.N. Oshinski et al.; "Two–Dimensional Coronary MR Angiography Without Breath Holding"; *Radiology* 201; pp. 737–743; (Dec. 1996).

C.R. Ramsey et al.; "A Comparison Of Beam Characteristics For Gated And Nongated Clinical X–Ray Beams"; *Med. Phys.* 26; pp. 2086–2091; (Oct. 1999).

C.R. Ramsey et al.; "Clinical Efficacy Of Respiratory Gated Conformal Radiation Therapy", *Medical Dosimety* 24; pp. 115–119; (1999).

F. Lethimonnier et al.; "Three–Dimensional Coronary Artery MR Imaging Using Prospective Real–Time Respiratory Navigator And Linear Phase Shift Processing: Comparison With Conventional Coronary Angiography", *Magn. Reson. Imaging* 17; pp. 1111–1120; (1999).

R.J. van Geuns et al.; "Magnetic Resonance Of The Coronary Arteries: Clinical Results From Three Dimensional Evaluation Of A Respiratory Gated Technique"; *Heart* 82; pp. 515–519; (Oct. 1999).

C.J. Ritchie et al.; "Predictive Respiratory Gating: A New Method To Reduce Motion Artifacts On CT Scans"; *Radiology* 190; pp. 847–852; (Mar. 1994).

R.D. Rogus et al.; "Accuracy Of A Photogrammetry–Based Patient Positioning and Monitoring System For Radiation Therapy"; *Med. Phys.* 26; pp. 721–728; (May 1999).

K. Cho et al.; "Development Of Respiratory Gated Myocardial SPECT System", *J. Nucl. Cardiol.* 6; pp. 20–28; (Jan./Feb. 1999).

C.S. Ross et al.; "Analysis Of Movement Of Intrathoracic Neoplasms Using Ultrafast Computerized Tomography"; *Int. J. Radiat. Oncol. Biol. Phys.* 18; pp. 671–677; (Mar. 1990).

V.M. Runge et al.; "Respiratory Gating In Magnetic Resonance Imaging at 0.5 Tesla"; *Radiology* 151; p. 521–523; (May 1984).

T.S. Sachs et al.; "Real–Time Motion Detection In Spiral MRI Using Navigators", *Magn. Reson. Med.* 32; pp. 639–645; (Nov. 1994).

L.H. Schwartz et al.; "Kidney Mobility During Respiration"; *Radiother. Oncol.* 32; pp. 84–86; (1994).

M. Paivansalo Suramo et al.; "Cranio–caudal Movements Of The Liver, Pancreas And Kidneys In Respiration", *Acta Radiol. Diagn.* 2; pp. 129–131; (1984).

C.R. Ramsey et al.; "Clinical Efficacy Of Respiratory Gated Conformal Radiation Therapy"; *Med. Dosim.* 24; pp. 115–119; (1999).

J.W. Wong et al.; "The Use Of Active Breathing Control (ABC) To Reduce Margin For Breathing Motion"; *Int. J. Radiat. Oncol., Phys.* 44; pp. 911–919; (Jul. 1999).

H.D. Kubo et al.; "Compatibility Of Varian 2100C Gated Operations With Enhanced Dynamic Wedge And IMRT Dose Delivery"; *Med. Phys.* 27; pp. 1732–1738; (Aug. 2000).

H. Shirato et al.; "Four–Dimensional Treatment Planning And Fluroscopic Real–Time Tumor Tracking Radiotherapy For Moving Rumor"; *Int. J. Radiat. Oncol., Biol., Phys.* 48; pp. 435–442; (Sep. 2000).

N.G. Bellenger et al.; "Left Ventricular Quantification In Heart Failure By Cardiovascular MR Using Prospective Respiratory Navigator Gating: Comparison With Breath–Hold Acquisition"; *J. Magn. Reson. Imaging* 11; pp. 411–417; (Apr. 2000).

Q. Yuan et al.; "Cardiac–Respiratory Gating Method For Magnetic Resonance Imaging Of The Heart"; *Magn. Reson. Med.* 43; pp. 314–318; (Feb. 2000).

K.E. Rosenzweig et al.; "The Deep Inspiration Breath Hold Technique In The Treatment Of Inoperable Non–Small Cell Lung Cancer"; *Int. J. Radiat. Oncol., Biol., Phys.* 48; pp. 81–87; (Aug. 2000).

D. Mah et al.; "Technical Aspects Of The Deep Inspiration Breath Hold Technique In The Treatment Of Thoracic Cancer"; *Int. J. Radiat. Oncol., Biol., Phys.* 48; pp. 1175–1185; (Nov. 2000).

G.S. Mageras et al.; "Respiratory Motion–Induced Treatment Uncertainties"; *Patras Medical Physics 99—VI International Conference On Medical Physics*, Monduzzi Editore; pp. 33–39; (Sep. 1999).

G.S. Mageras; "Interventional Strategies For Reducing Respiratory–Induced Motion In External Beam Therapy"; *The Use of Computers In Radiation Therapy XIIIth International Conference*, Heidelberg, Germany; pp. 514–516; (May 2000).

S. Malone et al.; "Respiratory–Induced Prostate Motion: Quantification And Characterization", *Int. J. Radiat. Oncol. Biol., Phys.* 48; pp. 105–109; (Aug. 2000).

G. Mageras et al.; "Initial Clinical Evaluation Of A Respiratory Gating Radiotherapy System"; $22^{nd}$ *Annual EMBS International Conference*, Chicago, IL.; pp. 2124–2127; (Jul. 23–28, 2000).

Ellen Yorke et al.; "Respiratory Gating Of Sliding Window IMRT"; $22^{nd}$ *Annual EMBS International Conference*, Chicago, IL.; pp. 2118–2121; (Jul. 23–28, 2000).

\* cited by examiner

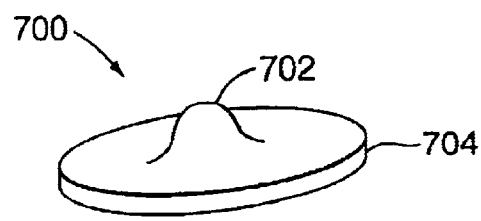
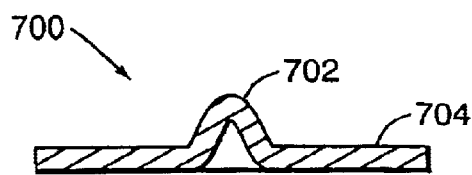
FIG. 7a          FIG. 7b
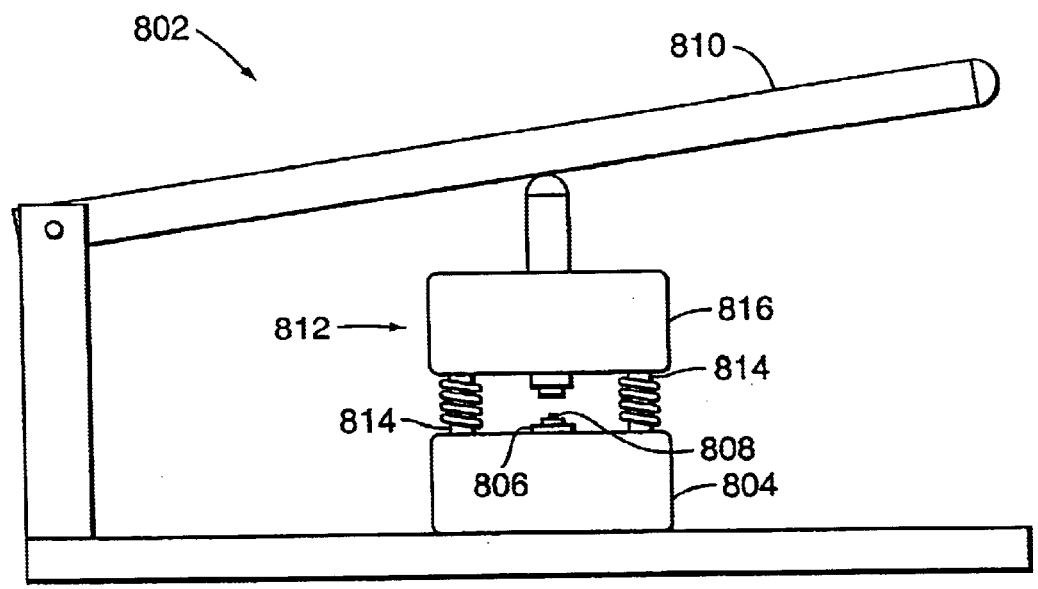
FIG. 8

METHOD AND SYSTEM FOR PHYSIOLOGICAL GATING OF RADIATION THERAPY

This application is a continuation of U.S. patent application Ser. No. 09/178,384, filed Oct. 23, 1998, now abandoned.

BACKGROUND OF THE INVENTION

1. Field of the Invention

The present invention relates to medical methods and systems. More particularly, the invention relates to a method and system for physiological gating of radiation therapy.

2. Background

Radiation therapy involves medical procedures that selectively expose certain areas of a human body, such as cancerous tumors, to high doses of radiation. The intent of the radiation therapy is to irradiate the targeted biological tissue such that the harmful tissue is destroyed. In certain types of radiotherapy, the irradiation volume can be restricted to the size and shape of the tumor or targeted tissue region to avoid inflicting unnecessary radiation damage to healthy tissue. For example, conformal therapy is a radiotherapy technique that is often employed to optimize dose distribution by conforming the treatment volume more closely to the targeted tumor.

Normal physiological movement represents a limitation in the clinical planning and delivery of conventional radiotherapy and conformal therapy. Normal physiological movement, such as respiration or heart movement, can cause a positional movement of the tumor or tissue region undergoing irradiation. If the radiation beam has been shaped to conform the treatment volume to the exact dimensions of a tumor, then movement of that tumor during treatment could result in the radiation beam not being sufficiently sized or shaped to fully cover the targeted tumoral tissue.

To address this problem, the size and/or shape of the radiation beam can be expanded by a "movement margin" (i.e., the predicted movement distance in any direction of the targeted tumor) to maintain full irradiation of the targeted tissue. The drawback to this approach is that this increased irradiation volume results in radiation being applied to otherwise healthy tissue that is located within the area of the expanded volume. In other words, motion during treatment necessitates the application of a radiation field of an expanded size that could negatively affect an unacceptably large volume of normal tissue surrounding the targeted treatment volume.

Another approach to this problem involves physiological gating of the radiation beam during treatment, with the gating signal synchronized to the movement of the patient's body. In this approach, instruments are utilized to measure the physiological state of the patient with reference to the particular physiological movement being examined. For example, respiration has been shown to cause movements in the position of a lung tumor in a patient's body. If radiotherapy is being applied to the lung tumor, then a temperature sensor, strain gauge or preumotactrograph can be attached to the patient to measure the patient's respiration cycle. The radiation beam can be gated based upon certain threshold points within the measured respiratory cycle, such that the radiation beam is disengaged during periods in the respiration cycle that correspond to excessive movement of the lung tumor.

Known methods for performing physiological gating typically require specialized instruments to be placed in contact with or invasively mounted on the patient. For instance, the known approaches to physiological gating synchronized with the respiratory cycle require a patient-contact instrument such as a strain gauge or spirometer to be attached to the patient's body. A known approach to gating synchronized to the cardiac cycle requires an electrocardiograph to be connected to the patient's body. Requiring an instrument to be placed in contact with, or invasively mounted in, the patient's body could cause problems under certain circumstances. For example, a spirometer is a pneumotachograph device that is mounted on a patient to measure the volume of air passing through the patient's airway during respiration. The discomfort associated with using a spirometer can limit the usefulness of that instrument in measuring a patient's respiration cycle, particularly if the gating procedure requires use of that instrument for an extended period of time. Moreover, many of these instruments have cumbersome wires or connections that limit the usability of these instruments within certain confined areas or with certain patient body configurations. Another drawback is that a specialized instrument is required for each body part that is being measured for movement. Not only does this require the use of a plurality of instruments for the multiplicity of body parts that may have to be measured for movement, but in some cases, the particular body part undergoing examination may not have an associated specialized instrument to detect its movement.

Therefore, there is a need for a system and method to address these and other problems of the related art. There is a need for a method and system of physiological gating which does not require instruments or probes to be mounted, either externally or invasively, on or in the patient's body. Moreover, there is a need for a method and system that can accurately and consistently allow planning for physiological gating of radiation treatments.

SUMMARY OF THE INVENTION

The present invention provides an improved method and system for physiological gating for radiation therapy. According to an aspect, the invention comprises the use of an optical or video imaging system to generate image data to measure regular physiological movement of a patient's body. An optical or video imaging system provides a non-invasive method for measuring motion on a patient's body. The image data can be used to quantify voluntary or involuntary motion of the patient that may affect the delivery of radiation to a target valve. A gating signal can be generated to suspend delivery of radiation upon certain threshold event detected in the motion cycle.

These and other aspects, objects, and advantages of the invention are described below in the detailed description, drawings, and claims.

BRIEF DESCRIPTION OF THE DRAWINGS

The accompanying drawings are included to provide a further understanding of the invention and, together with the Detailed Description, serve to explain the principles of the invention.

FIG. 6b depicts a front view of the camera of FIG. 6a.

FIG. 7a depicts a retro-reflective marker according to an embodiment of the invention.

FIG. 7b depicts a cross-sectional view of the retro-reflective marker of FIG. 7a.

FIG. 8 depicts an apparatus for making a retro-reflective marker.

DETAILED DESCRIPTION

Figure 1:
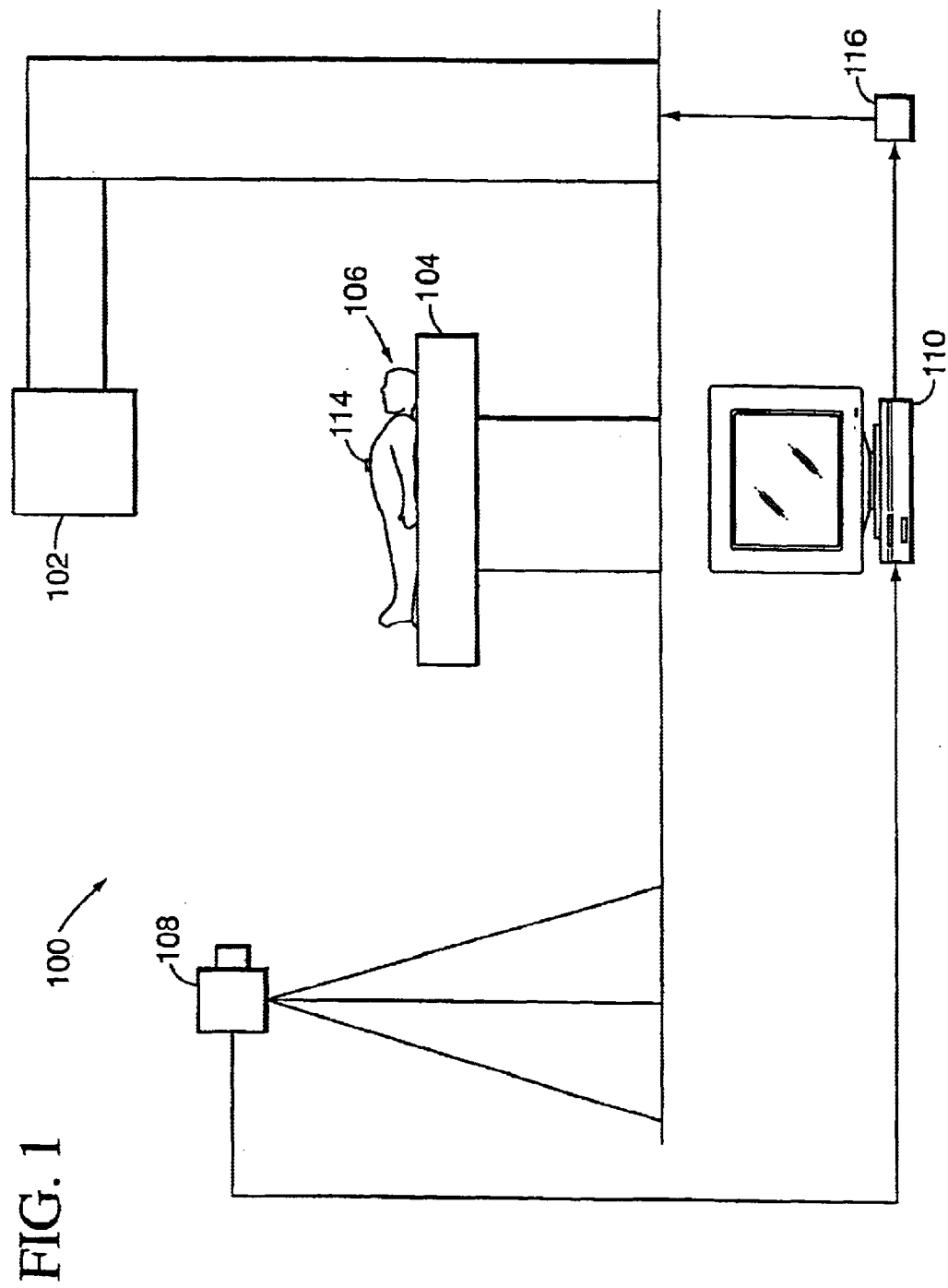
FIG. 1 depicts the components of a system for physiological gating according to an embodiment of the invention.

FIG. 1 depicts the components of a system 100 for physiological gating of radiation therapy according to an embodiment of the invention. System 100 comprises a radiation beam source 102 (such as a conventional linear accelerator) which is positionally configured to direct a radiation beam at a patient 106 located on treatment table 104. A switch 116 is operatively coupled to the radiation beam source 102. Switch 116 can be operated to suspend the application of the radiation beam at patient 106. In an embodiment, switch 116 is part of the mechanical and electrical structure of radiation beam source 102. Alternatively, switch 116 comprises an external apparatus that is connected to the control electronics of radiation beam source 102.

An optical or video image apparatus, such as video camera 108, is aimed such that as least part of the patient 106 is within the camera's field of view. Camera 108 monitors patient 106 for motion relating to the particular physiological activity being measured. For example, if respiration movements of the patient is being monitored, then camera 108 can be configured to monitor the motion of the patient's chest. According to an embodiment, camera 108 is placed with its axis at approximately 45 degrees to the longitudinal axis of the patient 106. For measurement of respiration activity that could result in about 3–5 mm of chest motion, the video image field of view is preferably set to view an approximately 20 cm by 20 cm area of the patient's chest. For purposes of illustration only, a single camera 108 is shown in FIG. 1. However, the number of cameras 108 employed in the present invention can exceed that number, and the exact number to be used in the invention depends upon the particular application to which it is directed.

In an embodiment, one or more illumination sources (which are infrared sources in the preferred embodiment) project light at the patient 106 on treatment table 104. The generated light is reflected from one or more landmarks on the patient's body. The camera 108, which is directed at patient 106, captures and detects the reflected light from the one or more landmarks. The landmarks are selected based upon the physiological activity being studied. For example, for respiration measurements, landmarks are selected from one or more locations on the patient's chest.

The output signals of camera 108 are sent to a computer 110 or other type of processing unit having the capability to receive video images. According to a particular embodiment, computer 110 comprises an Intel Pentium-based processor running Microsoft Windows NT and includes a video frame grabber card having a separate channel for each video source utilized in the system. The images recorded by camera 108 are sent to computer 110 for processing. If camera 108 produces an analog output, the frame grabber converts the camera signals to a digital signal prior to processing by computer 110. Based upon the video signals received by computer 110, control signals can be sent from computer 110 to operate switch 116.

According to one embodiment, one or more passive markers 114 are located on the patient in the area to be detected for movement. Each marker 114 preferably comprises a reflective or retro-reflective material that can reflect light, whether in the visible or invisible wavelengths. If the illumination source is co-located with camera 108, then marker 114 preferably comprises a retro-reflective material that reflects light mostly in the direction of the illumination source. Alternatively, each marker 114 comprises its own light source. The marker 114 is used in place of or in conjunction with physical landmarks on the patient's body that is imaged by the camera 108 to detect patient movement. Markers 114 are preferably used instead of body landmarks because such markers 114 are easier to detect and track via the video image generated by camera 108. Because of the reflective or retro-reflective qualities of the preferred markers 114, the markers 114 inherently provide greater contrast in a video image to a light detecting apparatus such as camera 108, particularly when the camera 108 and illumination source are co-located.

Utilizing a video or optical based system to track patient movement provides several advantages. First, a video or optical based system provides a reliable mechanism for repeating measurement results between uses on a given patient. Second, the method of the invention is noninvasive, and even if markers are used, no cables or connections must be made to the patient. Moreover, if the use of markers is impractical, the system can still be utilized without markers by performing measurements of physiological activity keyed to selected body landmarks. Finally, the method of the invention is more accurate because it is based upon absolute measurement of external anatomical physical movement.

A possible inefficiency in tracking the markers 114 is that the marker may appear anywhere on the video frame, and all of the image elements of the video frame may have to be examined to determine the location of the marker 114. Thus, in an embodiment, the initial determination of locations for the marker 114 involves an examination of all of the image elements in the video frame. If the video frame comprise 640 by 480 image elements, then all 307200 (640*480) image elements are initially examined to find the location of the markers 114.

For real-time tracking of the marker 114, examining every image element for every video frame to determine the location of the marker 114 in real-time could consume a significant amount of system resources. Thus, in an embodiment, the real-time tracking of marker 114 can be facilitated by processing a small region of the video frame, referred to herein as a "tracking gate", that is placed based on estimation of the location of the already-identified marker 114 in the video frame. The previously determined location of a marker 114 defined in the previous video frame is used to define an initial search range (i.e., the tracking gate) for that same marker in real-time. The tracking gate is a relatively small portion of the video frame that is centered at the previous location of the marker 114. The taracking gate is expanded only if it does not contain the new location of the marker 114. As an example, consider the situation when the previously determined location of a particular marker is image element (50, 50) in a video frame. If the tracking gate is limited to a 50 by 50 area of the video frame, then the tracking gate for this example would comprise the image elements bound within the area defined by the coordinates (25, 50), (75, 50), (50, 25), and (50, 75). The other portions of the video &me are searched only if the marker 114 is not found within this tracking gate.

Figure 2:
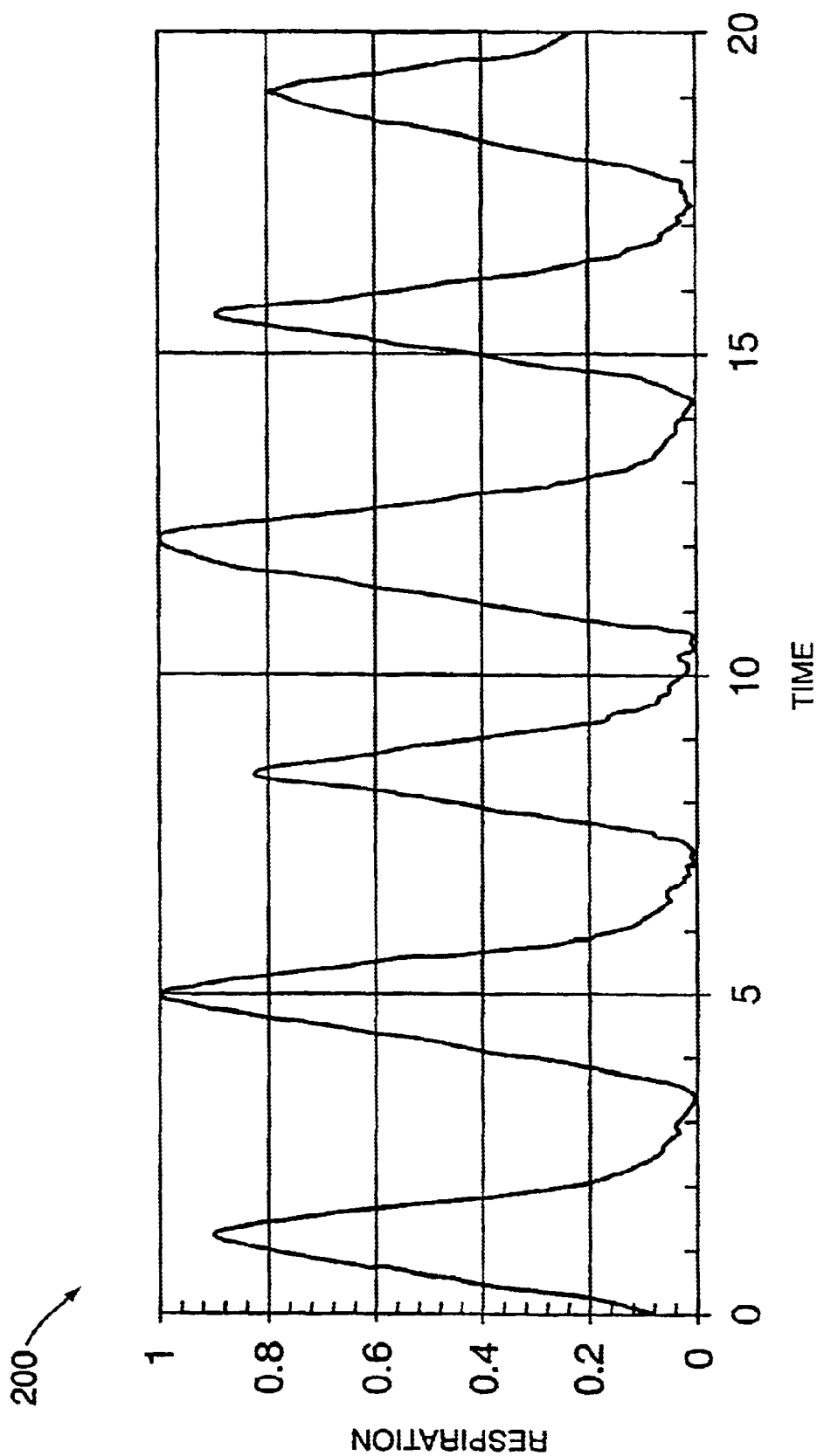
FIG. 2 depicts an example of a respiratory motion signal chart.

The video image signals sent from camera 108 to computer 110 arc used to generate and track motion signals representative of the movement of marker 114 and/or landmark structures on the patient's body. FIG. 2 depicts an example of a motion signal chart 200 for respiratory movement that contains information regarding the movement of marker 114 during a given measurement period. The horizontal axis represents points in time and the vertical axis represents the relative location or movement of the marker 114.

An important aspect of physiological gating of radiotherapy is the determination of the boundaries of the "treatment intervals" for applying radiation. For gating purposes, threshold points can be defined over the amplitude range of the motion signal to determine the boundaries of the treatment intervals. Motion of the patient that fall outside the boundaries of the treatment intervals correspond to movement that is predicted to cause unacceptable levels of movement to the tumor or tissue targeted for irradiation. According to an embodiment, the treatment intervals correspond to the portion of the physiological cycle in which motion of the clinical target volume is minimized. Other factors for determining the boundaries of the treatment intervals include identifying the portion of the motion signals involving the least movement of the target volume or the portion of the motion signal involving the largest separation of the target volume from organs at risk. Thus, the radiation beam pattern can be shaped with the minimum possible margin to account for patient movement.

Figure 3:
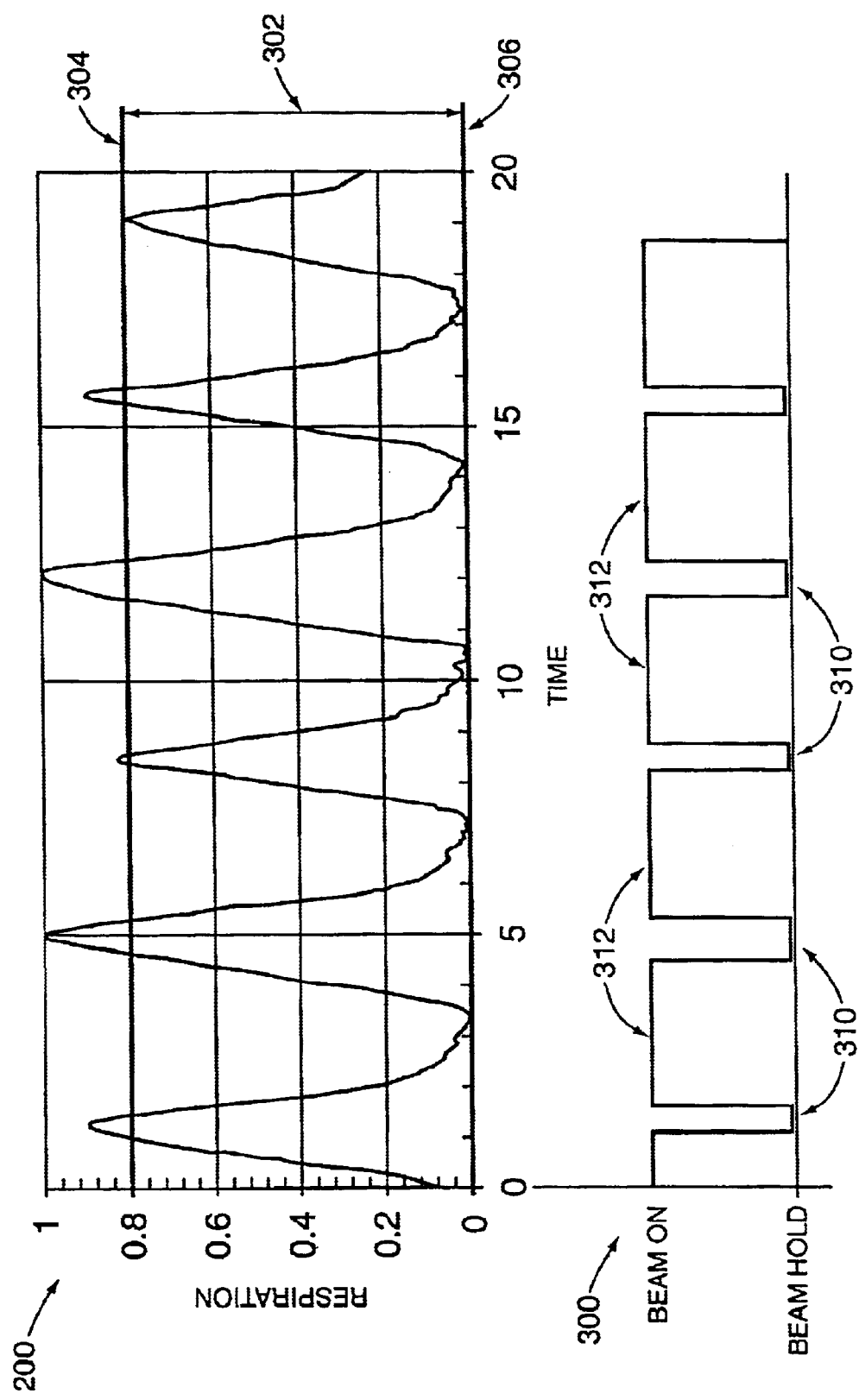
FIG. 3 depicts a motion signal chart and a gating signal chart.

Radiation is applied to the patient only when the motion signal is within the designated treatment intervals. Referring to FIG. 3, depicted are examples of treatment intervals, indicated by signal range 302, that has been defined over the motion data shown in motion signal chart 200. In the example of FIG. 3, any movement of the measured body location that exceeds the value of 0.8 (shown by upper boundary line 304) or which moves below the value of 0.0 (shown by lower boundary line 306) falls outside the boundaries of the treatment intervals.

Shown in FIG. 3 is an example of a gating signal chart 300 that is aligned with motion signal chart 200. Any motion signal that falls outside the treatment interval signal range 302 results in a "beam hold" gating signal threshold 310 that stops the application of radiation to the patient. Any motion signal that is within the treatment interval signal range 302 results in a "beam on" gating signal threshold 312 that allows radiation to be applied to the patient. In an embodiment, digital signals that represent the information shown in motion signal chart 200 are processed by computer 110 and compared to the threshold levels of the treatment interval signal range 302 to generate gating signal thresholds 310 and 312. Alternatively, gating signal thresholds 310 and 312 can be obtained by feeding analog motion signals to a comparator to be compared with analog threshold signals that correspond to treatment interval signal range 302. In any case, gating signal thresholds 310 and 312 are generated by computer 110 and are applied to the switch 116 that controls the operation of radiation beam source 102 (FIG. 1) to stop or start the application of a radiation beam at patient 106.

Figure 4:
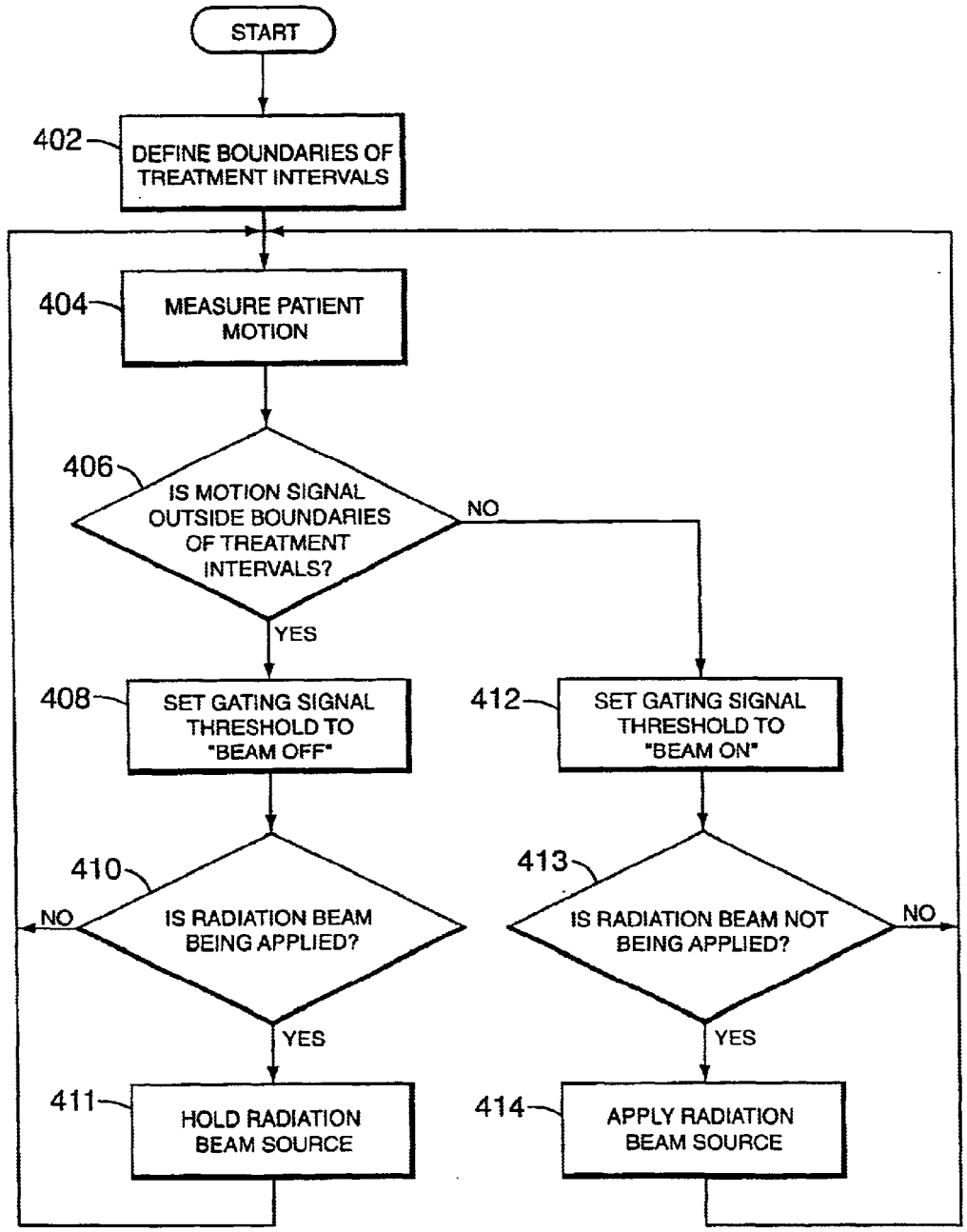
FIG. 4 is a flowchart showing process actions performed in an embodiment of the invention.

FIG. 4 is a flowchart of the process actions performed in an embodiment of the invention. The first process action is to define boundaries for the treatment intervals over the range of motion signals to be detected by a camera (402). As indicated above, any motion that fall outside the boundaries of the treatment intervals correspond to motion that is predicted to result in unacceptable levels of movement of the tumor or tissue targeted for irradiation. An optical or video imaging system, such as a video camera, is used to measure the physiological motion of the patient (404), and the output signals of the optical or video imaging system are processed to compare the measured motion signals with the threshold boundaries of the treatment intervals (406).

If the motion signal is outside the boundaries of the treatment intervals, then a "beam off" gating signal threshold is applied to a switch that is operatively coupled to the radiation beam source (408). If the radiation beam source is presently irradiating the patient (410), then the switch setting is operated to hold or stop the radiation beam (411). The process then returns back to process action 406.

If the motion signal is within the boundaries of the treatment intervals, then a "beam on" gating signal threshold is produced (412) and is applied to a switch that is operatively coupled to the radiation beam source. If the radiation beam source is presently not being applied to the patient (413), then the switch setting is operated to turn on or apply the radiation beam source to irradiate the patient (414). The process then returns back to process action 406.

According to one embodiment, the radiation beam source can be disengaged if a significant deviation is detected in the regular physiological movements of the patient. Such deviations can result from sudden movement or coughing by the patient. The position and/or orientation of the targeted tissue may unacceptably shift as a result of this deviation, even though the amplitude range of the motion signal still falls within the boundaries of the treatment intervals during this deviation. Thus, detection of such deviations helps define the appropriate time periods to gate the radiation treatment. A process for detecting deviations from regular physiological movements of a patient is disclosed in copending U.S. patent application Ser. No. 09/178,383, filed concurrently herewith, which is hereby incorporated by reference in its entirety.

Figure 5A:
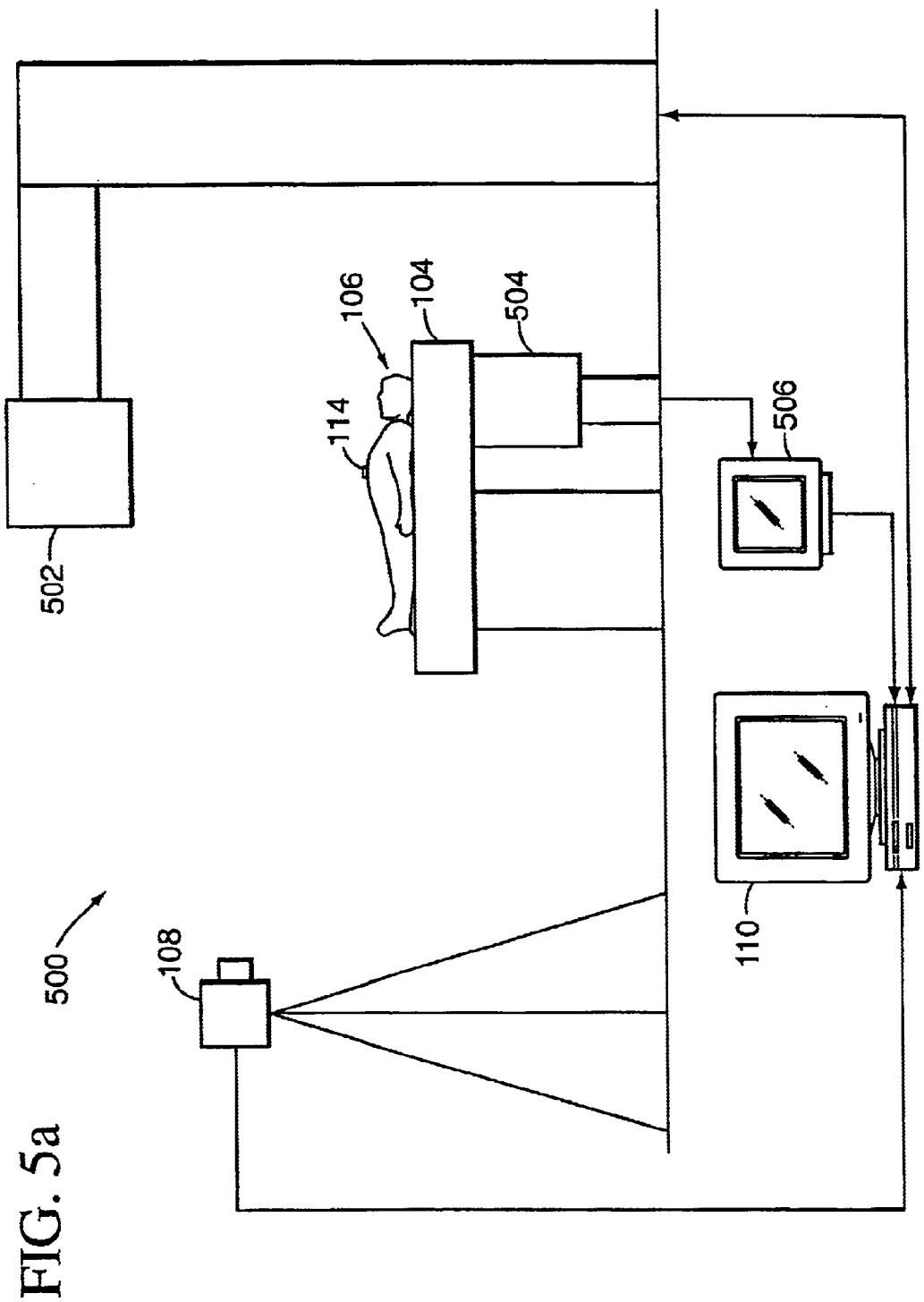
FIG. 5a depicts the components of a system for performing gating simulations according to an embodiment of the invention.

During the planning phase of the radiation treatment, gating simulations can be performed to determine the optimum boundaries of the treatment intervals. FIG. 5a depicts a system 500 that can be employed to perform gating simulation. As with the system 100 shown in FIG. 1, system 500 comprises a camera 108 that is directed at a patient on a treatment table 104. The output signals of camera 108 are sent to a computer 110 for processing. System 500 additionally includes an imaging system capable of generating images of internal structures within the patient's body. In an embodiment, system 500 comprises a digital fluoroscopic imaging system having an x-ray source 502 and fluoroscopic x-ray detection apparatus 504. The resulting fluoro video can be displayed on a fluoro display device 506. In addition, the output signals from the fluoroscopic x-ray detection apparatus 504 can be sent to the computer 110.

During gating simulation, the movement of one or more landmarks or markers 114 on the patient's body is optically measured using camera 108. The detected motion of the landmark or marker 114 results in the generation of motion signals according to the process discussed with reference to FIG. 2. While motion data is being collected, the fluoroscopic video system generates imaging data for the tumor or tissue that is targeted for irradiation. In an embodiment, the positional geometry of the fluoroscopic imaging system is configured to correspond to the projection geometry of the radiation beam source that will be used in applying radiation beams for treatment. This allows accurate simulation of the target volume to be achieved during actual treatment.

Figure 5B:
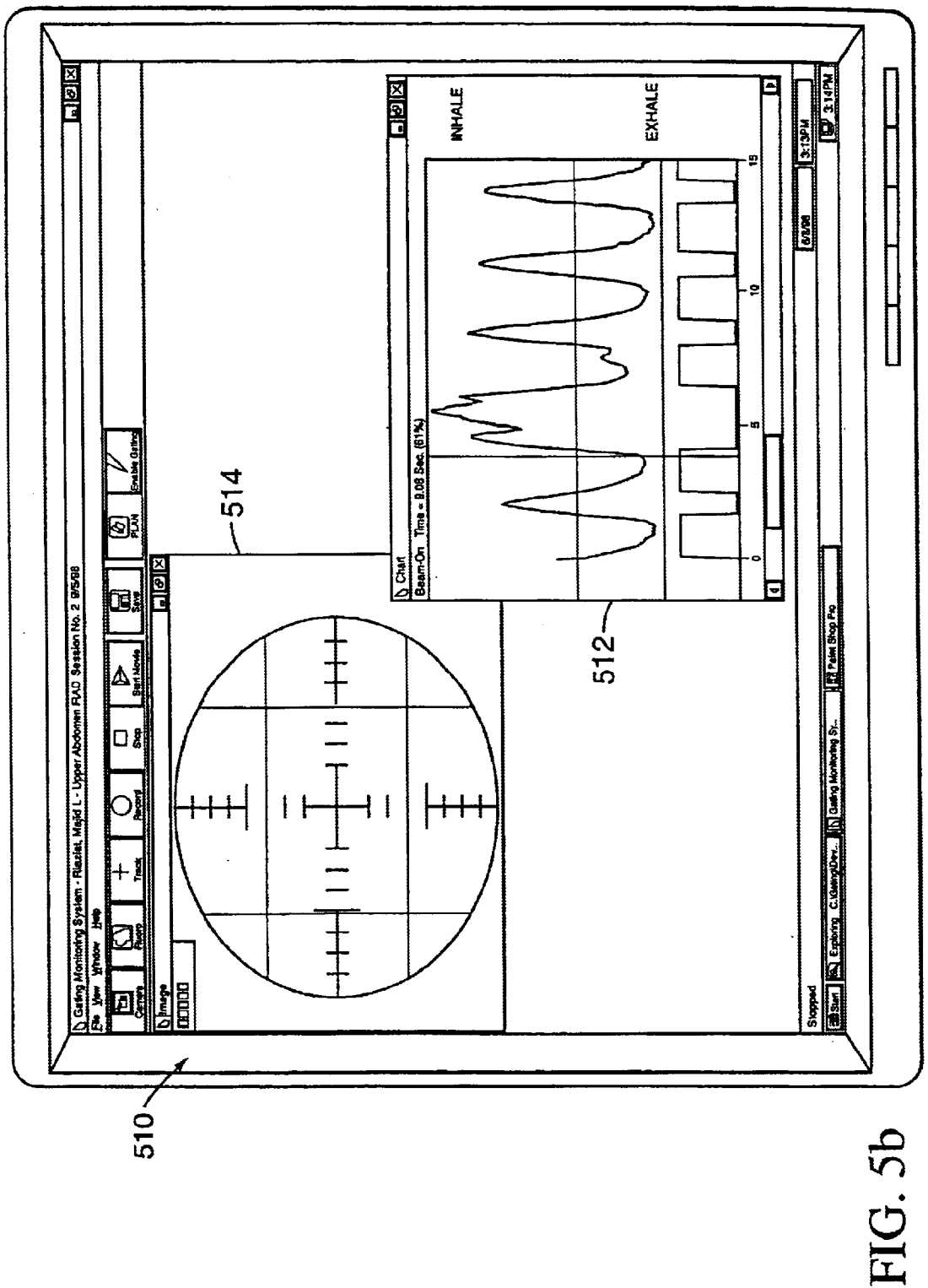
FIG. 5b depicts an embodiment of an user interface for gating simulation.

FIG. 5b depicts an embodiment of a user interface 510 for presenting the recorded data of the fluoro images and motion signals. A portion of user interface 510 displays a chart 512 of the measured motion signals. Another portion of user interface 510 displays a fluoro video 514. During the planning phase of treatment, the fluoro video 514 of the targeted tumor or tissue can be displayed in synchronization with the display of the motion signals. Simultaneous display of both sets of data allow a visual manner of determining the proper boundaries of the treatment intervals, based upon the range of movements of the tumor or target tissue during particular portions of the motion signals.

Gating simulations can be effected by performing "gated playback." Gated playback involves setting simulated threshold boundaries for the treatment intervals. During the gated playback, the user interface can be configured to only display the fluoro image when the motion signal is within the boundaries of the simulated treatment intervals. The fluoro video can be turned off or frozen if the motion signal is outside the simulated treatment intervals. The gating threshold can be dynamically adjusted while both the fluoro video and the motion signals are displayed in the user interface. The playback/adjustment procedure can be performed until the physician is satisfied with the gating thresholds of the treatment window. The display rate can be dynamically adjusted to speed or slow down the visual playback of the fluoro video.

In an embodiment, a visual display border can be formed around region(s) of interest in the fluoro video 514. For example, a box-like display border can be drawn around a tumor shown in fluoro video 514. Alternatively, a display border generally matching the shape of a tumor can be drawn around that tumor. The visual display border can be used to simulate the shape of an applied radiation beam. During playback, the movement of the tumor in relation to the visual display border at particular points in the motion signal range can help determine the proper boundaries of the treatment intervals.

The recorded fluoro image allows digital analysis and quantification of the amount of tumor motion resulting from regular physiological movement. For each image frame, the image data corresponding to the tumor or targeted tissue can be highlighted or otherwise selected by the computer 110. Calculations can be performed upon this image data to analyze motion of the tumor or tissue during the regular physiological movements.

According to an embodiment, this calculation can be performed by digital subtraction of image frames. When using digital subtraction, a first image frame is selected that corresponds to a first time point in a movement cycle. A second image frame is selected that corresponds to a second time point in the movement cycle. Digital subtraction is performed between the image elements of the first and second image frames to obtain the difference over the portion of the image frames corresponding to the tumor or targeted tissue. In an embodiment, the strength of the difference is computed using standard deviation of pixel values of the subtraction results. The distribution area over the area of subtraction is analyzed to determine the amount of positional movement experienced by the tumor or targeted tissue between the first and second time points in the movement cycle. This calculation can be performed over full recording periods to accurately quantify tumor or targeted tissue movement at various stages within the movement cycle.

The quantified movement data of the tumor or targeted tissue allows precise determination of gating thresholds for the treatment intervals. For example, if the physician desires the treatment intervals to include periods of movements that will not exceed a certain threshold movement margin, then the quantified movement data can be analyzed to determine the exact boundaries of the treatment intervals that achieves the desired movement margin. Alternatively, certain preset movement margin thresholds can be programmed into the computer 110. Based upon the preset movement margins, the system can perform an analysis of the movement data to determine the optimal gating thresholds of the treatment intervals to achieve the preset movement margins. This gating threshold can be designated as the default or suggested treatment intervals for the corresponding patient.

Verification can be performed to validate the gating threshold settings of the treatment intervals. This is particularly useful during delivery of fractionated treatment. This can be done as a second simulation procedure, by repeating the gating simulation employed during the planning phase. Alternatively, gated verification imaging can be performed during a treatment session scheduled for the patient with the radiation beam source. Gated electronic portal images can be obtained during delivery of the fractionated radiation treatments. To accomplish this, the gating system triggers a single exposure or a sequence of exposures which can be visually or automatically compared to the original reference images. The verification can be repeated at any point deemed clinically appropriate during the treatment schedule.

Figure 6A:
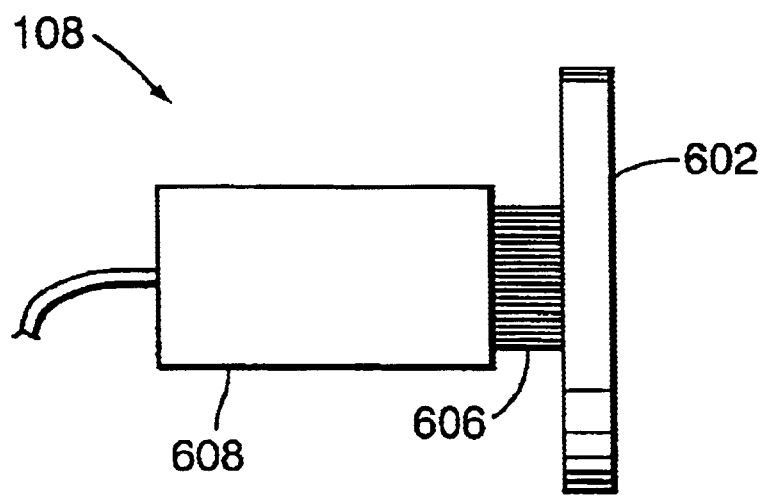
FIG. 6a depicts a side view an embodiment of a camera that can be utilized in the invention.
Figure 6B:
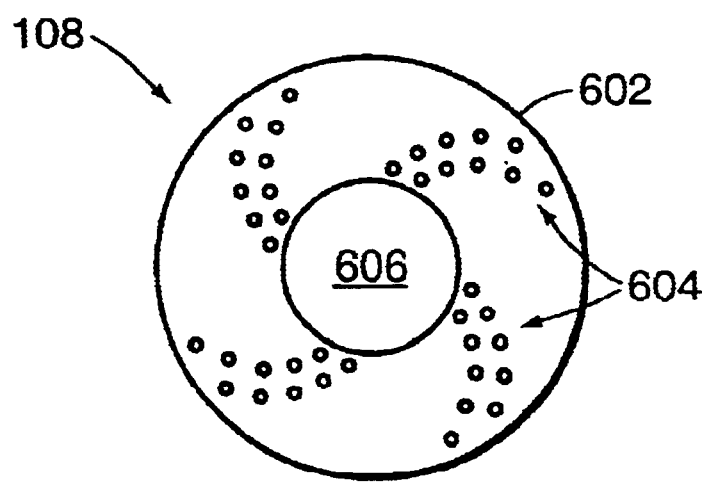

FIGS. 6a and 6b depict an embodiment of a camera 108 that can be used in the present invention. Camera 108 is a charge-couple device ("CCD") camera having one or more photoelectric cathodes and one or more CCD devices. A CCD device is a semiconductor device that can store charge in local areas, and upon appropriate control signals, transfers that charge to a readout point. When light photons from the scene to be images are focussed on the photoelectric cathodes, electrons are liberated in proportion to light intensity received at the camera. The electrons are captured in charge buckets located within the CCD device. The distribution of captured electrons in the charge buckets represents the image received at the camera. The CCD transfers these electrons to an analog-to-digital converter. The output of the analog-to-digital converter is sent to computer 410 to process the video image and to calculate the positions of the retro-reflective markers 406. According to an embodiment of the invention, camera 108 is a monochrome CCD camera having RS-170 output and 640×480 pixel resolution. Alternatively, camera 408 can comprise a CCD camera having CCIR output and 756×567 pixel resolution.

In a particular embodiment of the invention, an infra-red illuminator 602 ("IR illuminator") is co-located with camera 108. IR illuminator 602 produces one or more beams of infrared light that is directed in the same direction as camera 108. IR illuminator 602 comprises a surface that is ringed around the lens 606 of camera body 608. The surface of IR illuminator 602 contains a plurality of individual LED elements 604 for producing infrared light. The LED elements 604 are arranged in a spiral pattern on the IR illuminator 602. Infrared filters that may be part of the camera 108 are removed or disabled to increase the camera's sensitivity to infrared light.

According to an embodiment, digital video recordings of the patient in a session can be recorded via camera 108. The same camera 108 used for tracking patient movement can be used to record video images of the patient for future reference. A normal ambient light image sequence of the patient can be obtained in synchronization with the measured movement signals of markers 114.

FIGS. 7a and 7b depict an embodiment of a retro-reflective marker 700 that can be employed within the present invention. Retro-reflective marker 700 comprises a raised reflective surface 702 for reflecting light. Raised reflective surface 702 comprises a semi-spherical shape such that light can be reflected regardless of the input angle of the light source. A flat surface 704 surrounds the raised reflective surface 702. The underside of flat surface 704 provides a mounting area to attach retro-reflective marker 700 to particular locations on a patient's body. According to an embodiment, retro-reflective marker 700 is comprised of a retro-reflective material 3M#7610WS available from 3M Corporation. In an embodiment, marker 700 has a diameter of approximately 0.5 cm and a height of the highest point of raised reflective surface 702 of approximately 0.1 cm.

FIG. 8 depicts an apparatus 802 that can be employed to manufacture retro-reflective markers 700. Apparatus 802 comprises a base portion 804 having an elastic ring 806 affixed thereto. Elastic ring 806 is attached to bottom mold piece 808 having a bulge protruding from its center. A control lever 810 can be operated to move top portion 812 along support rods 814. Top portion 812 comprises a spring-loaded top mold piece 814. Top mold piece 814 is formed with a semi-spherical cavity on its underside. In operation, a piece of retro-reflective material is placed on bottom mold piece 808. Control lever 810 is operated to move top portion 812 towards base portion 804. The retro-reflective material is compressed and shaped between the bottom mold piece 808 and the top mold piece 814. The top mold piece 814 forms the upper exterior of the retro-reflective material into a semi-spherical shape.

In an alternate embodiment, marker 114 comprises a marker block having one or more reference locations on its surface. Each reference location on the marker block preferably comprises a retro-reflective or reflective material that is detectable by an optical imaging apparatus, such as camera 108.

Figure 9:
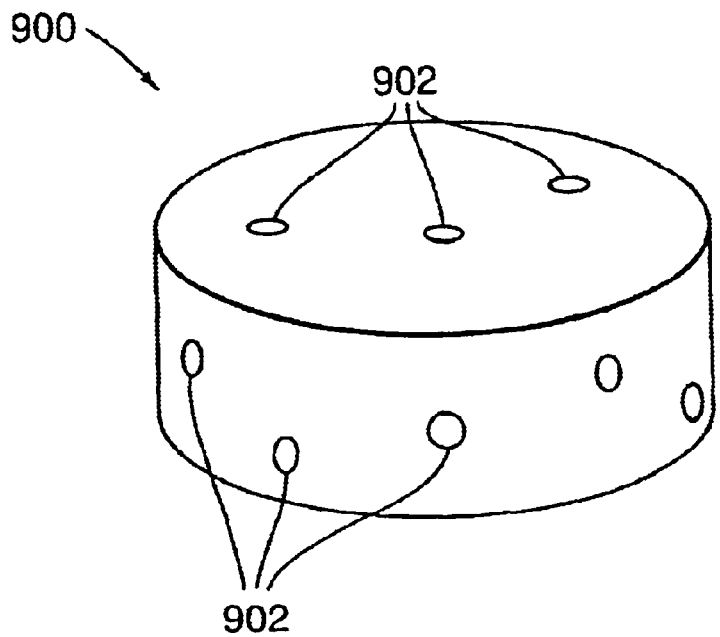
FIG. 9 depicts an embodiment of a marker block.

FIG. 9 depicts an embodiment of a marker block 900 having a cylindrical shape with multiple reference locations comprised of retro-reflective elements 902 located on its surface. Marker block 900 can be formed as a rigid block (e.g., from Styrofoam). Blocks made in this fashion can be reused a plurality of times, even with multiple patients. The retro-reflective elements 902 can be formed from the same material used to construct retro-reflective markers 114 of FIGS. 7a and 7b. The marker block is preferably formed from a material that is light-weight enough not to interfere with normal breathing by the patient.

Figure 10:
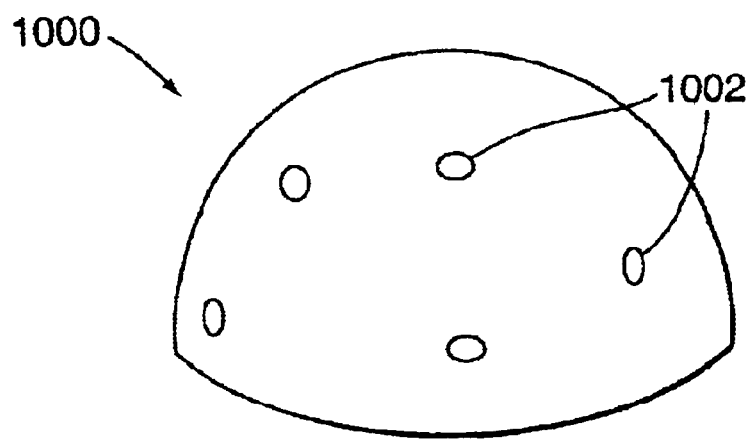
FIG. 10 depicts an alternate marker block.

A marker block can be formed into any shape or size, as long as the size, spacing, and positioning of the reference locations are configured such that a camera or other optical imaging apparatus can view and generate an image that accurately shows the positioning of the marker block. For example, FIG. 10 depicts an alternate marker block 1000 having a hemispherical shape comprised of a plurality of retro-reflective elements 1002 attached to its surface.

The marker block can be formed with shapes to fit particular body parts. For example, molds or casts that match to specific locations on the body can be employed as marker blocks. Marker blocks shaped to fit certain areas of the body facilitate the repeatable placement of the marker blocks at particular locations on the patient. Alternatively, the marker blocks can be formed to fit certain fixtures that are attached to a patient's body. For example, a marker block can be formed within indentations and grooves that allow it to be attached to eyeglasses. In yet another embodiment, the fixtures are formed with integral marker block(s) having reflective or retro-reflective markers on them.

An alternate embodiment of the marker block comprises only a single reference location/reflective element on its surface. This embodiment of the marker block is used in place of the retro-reflective marker 406 to detect particular locations on a patient's body with an optical imaging apparatus.

In the foregoing specification, the invention has been described with reference to specific embodiments thereof. It will, however, be evident that various modifications and changes may be made thereto without departing from the broader spirit and scope of the invention. For example, the operations performed by computer 110 can be performed by any combination of hardware and software within the scope of the invention, and should not be limited to particular embodiments comprising just a particular definition of "computer". The specification and drawings are, accordingly, to be regarded in an illustrative rather than restrictive sense.

What is claimed is:

1. A system for determining one or more treatment intervals for radiation therapy comprising:
   an imaging system for generating image data representative of an internal region of a patient's body;
   an instrument for generating motion information relating to physiological movement of the patient's body; and
   a user interface configured to synchronously display in a single display the image data with a motion signal chart the motion signal chart presenting a representation of the motion information and representing physiological movement during a measurement time period;
   wherein the user interface is further configured for allowing a gating signal chart to be determined based on the image data and the motion signal chart, the gating signal chart representing one or more treatment intervals.

2. The system of claim 1 in which the imaging system comprises a fluoroscopic imaging system.

3. The system of claim 1 in which the instrument comprises one or more cameras configured to detect the physiological movement.

4. The system of claim 1 in which a simulated treatment interval is defined over the motion information, and in which the image data is displayed during the simulated treatment interval.

5. The system of claim 4 in which the simulated treatment interval is dynamically adjustable.

6. The system of claim 1 further comprising a processor for generating digital analysis signals, the digital analysis signals comprising results of digital analysis to quantify motion of an internal structure shown in the image data.

7. The system of claim 6, wherein the processor is configured to generate the digital analysis signals by performing digital subtraction of image frames.

8. The system of claim 1, wherein the single display comprises a monitor screen.

9. The system of claim 8, wherein the monitor screen comprises a first region for displaying a representation of the image data, and a second region for displaying the motion signal chart.

10. A system for determining one or more treatment intervals in a planning phase of a treatment, comprising:
   means for recording image data representative of internal tissue targeted for irradiation;
   means for generating motion data representative of physiological movement of a patient;
   means for synchronously displaying in a single display the image data with a motion signal chart, the motion signal chart presenting a representation the generated motion data and representing physiological movement during a measurement time period; and
   means for determining a gating signal chart based on the image data and the motion signal chart, the gating signal chart representing one or more treatment intervals.

11. The system of claim 10, further comprising means for setting a desired boundary for the treatment interval.

12. The system of claim 11, wherein the means for displaying is configured to display the image data only when the motion data is within the desired boundary of the treatment interval.

13. The system of claim 11, wherein the means for setting comprises a user interface in which a user can set a border around a region of interest in an image.

14. The system of claim 13, wherein the border has a shape of a box.

15. The system of claim 13, wherein the border has a shape that resembles that of a tumor.

16. The system of claim 10, further comprising means for analyzing motion of a tissue during the physiological movement.

17. The system of claim 16, wherein the means for analyzing is configured to perform digital subtraction of image frames.

18. The system of claim 10, further comprising
   means for providing a preset movement margin threshold; and
   means for analyzing the motion data to determine an optimal gating threshold of the treatment interval to achieve the preset movement margin threshold.

19. The system of claim 10, further comprising means for performing verification to validate a gating threshold setting of the treatment interval.

20. The system of claim 10, wherein the means for recording image data comprises means for recording video data.

21. The system of claim 10, wherein the means for recording image data comprises means for obtaining a static image.

22. The system of claim 10, wherein the means for recording image data comprises means for configuring a positional geometry of an imaging system to correspond to a projection geometry of a radiation beam source.

23. The system of claim 10, wherein the means for synchronously displaying comprises a monitor screen.

24. The system of claim 23, wherein the monitor screen comprises a first region for displaying a representation of the image data, and a second region for displaying the motion signal chart.

25. A method for determining one or more treatment intervals for radiation therapy comprising:
   recording image data representative of internal tissue targeted for irradiation;
   generating motion data representative of a physiological movement that occurs while image data is being recorded;
   synchronously displaying the image data with a motion signal chart, the motion signal chart presenting a representation of the generated motion data and representing physiological movement during a measurement time period; and
   determining a gating signal chart based on the image data and the motion signal chart, the gating signal chart representing one or more treatment intervals.

26. The method of claim 25, wherein the determining comprises selecting a simulated treatment interval and displaying the image data only when the motion data is within the simulated treatment interval.

27. The method of claim 26 in which the image data is frozen when the motion data is outside the simulated treatment interval.

28. The method of claim 26 further comprising:
   adjusting the simulated treatment interval to view a different quantity of image data.

29. The method of claim 25 further comprising:
   analyzing the image data to quantify an amount of motion of the targeted tissue during the physiological movement.

30. The method of claim 25 further comprising:
   forming a display border around a region of the image data.

31. The method of claim 25 further comprising:
   verification of a gating threshold settings of the treatment interval by comparing gated radiation images with reference images created during a planning phase.

32. The method of claim 31 wherein the verification can be performed prior to or at any point during a radiation treatment session.

33. The method of claim 25, wherein the recording image data comprises recording video data.

34. The method of claim 25, wherein the recording image data comprises obtaining a static image.

35. The method of claim 25, wherein the recording image data comprises configuring a positional geometry of an imaging system to correspond to a projection geometry of a radiation beam source.

36. The method of claim 25, wherein the physiological movement comprises chest movement.

37. A method for determining one or more treatment intervals a planning phase of a treatment, comprising:
   recording image data representative of internal tissue targeted for irradiation;
   generating motion data representative of physiological movement of a patient;
   synchronously displaying the image data with a motion signal chart, the motion signal chart presenting a representation of the generated motion data and representing physiological movement during a measurement time period; and
   determining a gating signal chart based on the image data and the motion signal chart, the gating signal chart representing one or more treatment intervals.

38. The method of claim 37, further comprising setting a desired boundary for the treatment interval.

39. The method of claim 38, wherein the image data is displayed only when the motion data is within the desired boundary of the treatment interval.

40. The method of claim 38, wherein the setting comprises forming a border around a region of interest in a display.

41. The method of claim 40, wherein the border has a shape of a box.

42. The method of claim 40, wherein the border has a shape that resembles that of a tumor.

43. The method of claim 37, wherein the determining is performed based on a portion of the motion data.

44. The method of claim 43, wherein the physiological movement comprises chest movement.

45. The method of claim 37, further comprising analyzing motion of a tissue during the physiological movement.

46. The method of claim 45, wherein the analyzing comprises performing digital subtraction of image frames.

47. The method of claim 37, further comprising providing a preset movement margin threshold; and analyzing the motion data to determine an optimal boundary of the treatment interval to achieve the preset movement margin threshold.

48. The method of claim 37, further comprising performing verification to validate a gating threshold setting of the treatment interval.

49. The method of claim 37, wherein the recording image data comprises recording video data.

50. The method of claim 37, wherein the recording image data comprises obtaining a static image.

51. The method of claim 37, wherein the recording image data comprises configuring a positional geometry of an imaging system to correspond to a projection geometry of a radiation beam source.

52. The method of claim 37, wherein the determining comprises selecting a simulated treatment interval, and displaying the image data only when the motion data is within the simulated treatment interval.

53. The method of claim 52, wherein the determining further comprises freezing the image data when the motion data is outside the simulated treatment interval.

* * * * *